United States Patent [19]
Prakash et al.

[11] Patent Number: 5,973,209
[45] Date of Patent: *Oct. 26, 1999

[54] METHOD FOR PREPARING 3, 3-DIMETHYBUTYRALDEHYDE

[75] Inventors: Indra Prakash, Hoffman Estates; Marie-Christine D. Chapeau, Chicago, both of Ill.

[73] Assignee: The NutraSweet Company, Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/893,562

[22] Filed: Jul. 11, 1997

[51] Int. Cl.$^6$ .......................... C07C 45/00; C07D 301/03
[52] U.S. Cl. .......................... 568/483; 549/523; 549/529; 549/531; 549/532
[58] Field of Search .................................... 549/523, 529, 549/531, 532; 568/483

[56] References Cited

U.S. PATENT DOCUMENTS

| | | |
|---|---|---|
| 2,660,609 | 11/1953 | Robeson et al. . |
| 3,265,716 | 8/1966 | Dickey et al. . |
| 4,517,386 | 5/1985 | Naipawer . |
| 5,480,668 | 1/1996 | Nofre et al. . |
| 5,510,508 | 4/1996 | Claude et al. . |
| 5,770,775 | 6/1998 | Katritzky et al. . |

FOREIGN PATENT DOCUMENTS

| | | |
|---|---|---|
| 326 392 | 8/1989 | European Pat. Off. . |
| 763914 | 11/1933 | France . |
| 29 62 755 A1 | 7/1981 | Germany . |

OTHER PUBLICATIONS

Smith, J.G., Synthesis, 629–656 (1984).
Sudha, R., et al., J. Org. Chem. 61, 1877–79 (1996).
Lemini, C., et al., Synth. Commun. 25, 2695–2702 (1995).
Rickborn, B., Comprehensive Organic Synthesis, ed. B.M. Trost, I. Fleming and G. Pattenden, Pergamon, Oxford, 1991, vol. 3, pp. 733–775.
House, H., J. Amer. Chem. Soc. 77, 5083 (1955).
Rickborn, B. & Gerkin, R.M., J. Am. Chem. Soc. 93, 1963 (1971).
Baumstark, A.L., et al. Amer. Chem. Soc. 53, 3437–3439 (1988).

*Primary Examiner*—Alan Siegel
*Attorney, Agent, or Firm*—Fitzpatrick, Cella, Harper & Scinto

[57] ABSTRACT

A method is disclosed for preparing 3,3-dimethylbutyraldehyde by using silica gel to isomerize 3,3-dimethyl-1,2-epoxybutane, which in turn may be prepared by oxidation of dimethylbutene. Also disclosed is a method for oxidizing dimethylbutene with dimethyldioxirane to form 3,3-dimethyl-1,2-epoxybutane. The methods provide an economical means of preparing 3,3-dimethylbutyraldehyde.

13 Claims, No Drawings

METHOD FOR PREPARING 3,3-DIMETHYBUTYRALDEHYDE

BACKGROUND OF THE INVENTION

1. Field of the Invention

This invention relates to a method for preparing 3,3-dimethylbutyraldehyde in a highly economical manner by regioselective isomerization of vaporized 1,2-epoxy-3,3-dimethylbutane in the presence of silica gel. The invention also relates to a method for preparing 1,2-epoxy-3,3-dimethylbutane from 3,3-dimethylbutene by oxidation with dimethyldioxirane.

2. Related Background Art

Rearrangement of epoxides to carbonyl compounds has long been known. See, e.g., Smith, J. G. Synthesis, 629 (1984). For example, epoxides have been converted to aldehydes in a regiospecific manner through the use of lithium perchlorate in dimethyl ether (LPDE). Sudha, R., et al. J. Org. Chem. 61, 1877 (1996). However, this reference discloses that acyclic terminal olefin epoxides, such as 1,2-epoxyhexane did not react in the LPDE medium.

Yet another example is provided by Lemini, C., et al., Synth. Commun. 25, 2695 (1995) which report the transformation of arylmonosubstituted and 2-aryl, 2-methyl disubstituted oxiranes to aldehydes using silica gel as a reagent in solution under very mild conditions. U.S. Pat. No. 2,660,609 is directed to the isomerization of alkylene oxides such as ethylene oxide, 1,2-propylene oxide or 1,2 butylene oxide to aldehydes in the vapor phase using silica gel or fuller's earth in a fluidized form. However, these references do not disclose or suggest the regiospecific isomerization of 3,3-dimethylbutyraldehyde with silica gel.

Moreover, the latter reference also describes the formation of ketones and alcohols along with aldehydes in the isomerization of 1,2-epoxyalkanes with silica. The rearrangement gives different products (aldehydes, ketones, or alcohols) depending upon the reagents, reaction conditions and substituents (reviews on the isomerization of epoxides to aldehydes: J. G., Synthesis 1984, 637; Rickborn, B. in Comprehensive Organic Synthesis, ed. B. M. Trost, I. Fleming and G. Pattenden, Pergamon, Oxford, 1991, vol. 3, p. 733–775). Therefore, the behavior of the tert-butyl group is not predictable from that of the straight or other branched chain alkanes. For example, rearrangement of 1,2-epoxyalkanes (House, H., J. Amer. Chem. Soc. 1955, 77, 5083; where R is alkyl group) with boron trifluoride etherate gives only aldehyde and no ketone, whereas when R is a tert-butyl group, a mixture of products or the starting material are recovered (unpublished results). With LiBr-basic alumina only ketone, pinacolone, is formed (unpublished results). The effect of alkyl groups in the rearrangement of 1,2-epoxyalkanes using LiBr-HMPA is also observed by Rickborn and Gerkin (Rickborn, B. and Gerkin, R. M., J. Am. Chem. Soc. 1971, 93, 1693). Therefore, the conditions effective for n-alkyl or certain branched chain alkyl groups would not necessarily be expected to be effective for the tert-butyl group.

3,3-Dimethylbutyraldehyde is an intermediate that is useful in the preparation of the sweetener N-[N-(3,3-dimethylbutyl)-L-α-aspartyl]-L-phenylalanine disclosed in U.S. Pat. No. 5,480,668 and U.S. Pat. No. 5,510,508. Accordingly, a method for preparing that intermediate which is both economical and specific is highly desired.

SUMMARY OF THE INVENTION

This invention relates to a method for preparing 3,3-dimethylbutyraldehyde comprising the step of isomerizing vaporized 3,3-dimethyl-1,2-epoxybutane in the presence of silica gel. The invention also relates to the above-described method further comprising the step of oxidizing 3,3-dimethylbutene to form 3,3-dimethyl-1,2-epoxybutane prior to the step of isomerization. Yet another embodiment of this invention relates to the method of preparing 3,3-dimethyl-1,2-epoxybutane by treating 3,3-dimethylbutene with dimethyldioxirane.

The method of this invention allows for the preparation of 3,3-dimethylbutyraldehyde in a reproducible and highly economical manner so that use of the aldehyde in the preparation of a sweetener derived from aspartame is commercially practicable.

DETAILED DESCRIPTION OF THE INVENTION

The method of the invention provides a means for the regiospecific isomerization of vaporized 3,3-dimethyl-1,2-epoxybutane to form 3,3-dimethylbutyraldehyde through the use of silica gel.

Exemplary silica gels include Merck silica gels, grade 60, grade 7754, grade 10180 and grade 10184 available from Aldrich Chemical Co., Milwaukee, Wis. Typically, the silica gels have about a 70 to about a 230 mesh size.

The preparation of 3,3-dimethylbutyraldehyde comprises mixing 3,3-dimethyl-1,2-epoxybutane with silica gel for a period of time and at a sufficient pressure and temperature to form 3,3-dimethylbutyraldehyde in the vapor phase. Generally, the temperature of the reaction is between about 200° C. to about 400° C. and the reaction pressure, which will be dependent on the head space of the reaction vessel, is typically elevated, for example, to about 500 to 850 psi, preferably about 650 to 750 psi. The reaction time is typically held between about 2 and about 72 hours.

The reaction is generally carried out by mixing 1,2-epoxy-3,3-dimethylbutane with silica gel in a reaction vessel. Useful reaction vessels are well known to those of ordinary skill in the art and can be of varying size depending on production needs. Generally the weight ratio of silica gel to 3,3-dimethyl-1,2-epoxybutane will be in a range from about 10:1 to about 1:1 preferably about 5:1 to about 3:1. Typically the reaction mixture will be flushed with an inert gas, such as argon, followed by heating and stirring to the desired temperature and pressure to vaporize the 1,2-epoxy-3,3-dimethylbutane.

In a preferred embodiment of this invention, the method includes the step of preparing 3,3-dimethyl-1,2-epoxybutane by oxidation of dimethylbutene prior to the step of isomerization. This two step synthesis is illustrated below.

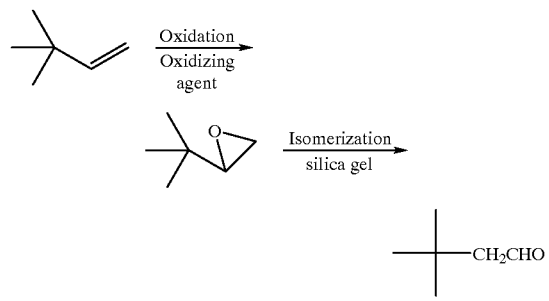

The step of oxidation is typically accomplished by exposing 3,3-dimethylbutene to an oxidizing agent. Preferred oxidizing agents includes dimethyldioxirane, oxygen, peroxide, NaOCl and peracids. Exemplary peracids include without limitation perbenzoic acid, metachlorobenzoic acid, monoperoxyphthalic acid, trifluoroperacetic acid, magnesium monoperoxyphthalate, peracetic acid. Other oxidizing reagents include peroxides such as, for example, hydrogen peroxide, t-butylhydroperoxide and dibenzoylperoxide. A particularly preferred oxidizing agent is dimethyldioxirane. Generally, the oxidizing agent is present in an amount between about 1.0 to about 1.05 percent by molar weight of the dimethylbutene. Typically, the step of oxidation is started at a temperature of between about −5° C. to about 0° C. and at atmospheric pressure and conducted at about 22–25° C. with a reaction time of about 24 hours.

Yet another embodiment of this invention comprises a method of forming 3,3-dimethyl-1,2-epoxybutane through oxidation of 3,3-dimethylbutene with dimethyldioxirane. Oxidation of 3,3-dimethylbutene with dimethyldioxirane may be preferably accomplished through the in situ generation of dimethyldioxirane by the reaction of acetone with "Oxone"(potassium peroxymonosulfate available from E.I. Du Pont de Nemours & Company, Wilmington, Del.). In such a case the Oxone and acetone are generally admixed in a molar ration of about 1:5 to about 1:9 in combination with 3,3-dimethylbutene.

The Examples which follow are intended as an illustration of certain preferred embodiments of the invention, and no limitation of the invention is implied.

Example 1

Synthesis of 1,2-epoxy-3,3-dimethyl butane

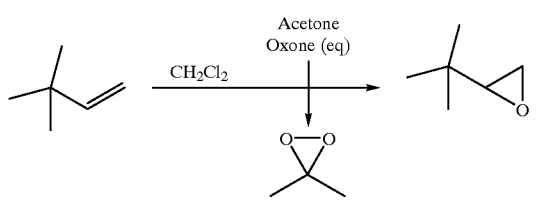

A solution of potassium monopersulfate (Oxone, 4.08 g; 16.1 mmol) and EDTA (ca. 200 mg) dissolved in distilled water (100 mL), was added to a biphasic system of 0.60 M $KH_2PO_4/Na_2HPO_4$ buffer solution (200 mL, pH 7.5), $CH_2Cl_2$ (300 mL), acetone (8.3 mL, 0.113 mole), 18-crown-6 (1,4,7,10,13,16-hexaoxacyclooctadeane) which was used as a phase transfer catalyst, (2.5 g; 9.46 mmol), and 3,3-dimethyl butene (1.29 mL; 0.84 g; 10 mmol). All solutions were kept at 0° C. prior to addition; the resulting mixture was stirred at 0° C. for one hour, then allowed to warm up to room temperature, and stirred for 22 hr. After this time, the reaction mixture was transferred in a separatory funnel, and the organic layer separated. The aqueous phase was extracted three times with $CH_2Cl_2$ (150 mL ea.). The combined $CH_2Cl_2$ solutions were dried over $MgSO_4$, filtered, concentrated by distillation to a small volume (50 to 65 mL), analyzed and quantified by gas chromatography (GC). Yield 75 to 77.1% (751.5 to 772.7 mg; 7.50 to 7.71 mmol). $^1$H-NMR($CDCl_3$): 0.86 (9H t-Bu), 2.55 (2H, $CH_2$), 2.66 (1H, CH); $^{13}$C-NMR ($CDCl_3$): 24.7, 29.7, 43.2, 59.2.

Example 2

Epoxide rearrangement using silica gel as catalyst

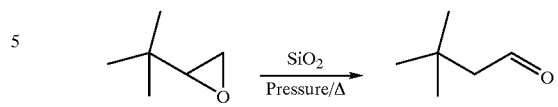

In a cool Parr Reactor, was placed 1,2-epoxy-3,3-dimethylbutane (10 g; 99.8 mmol). The reactor was placed on a dry ice bath and slowly 40 g of silica gel was added. The reactor was closed and flushed to 50 PSI twice with argon. Stirring and heating were then applied and followed closely. As the temperature increased, the pressure in the reactor increased as well. The maximum pressure applied was calculated to be 735 PSI and the optimum temperature between 200 to 400° C. At a temperature of 300 to 310° C., the pressure reached 700–710 PSI and the reactor was kept under these conditions for the remaining reaction time. Different reaction times were investigated: 1 day and 3 days. The conversion was analyzed by GC. To do that, at the desired time, the stirring was stopped and the reactor placed on dry ice until the pressure dropped to 10–50 PSI. The gas valve was opened and pressure released (no 3,3-dimethylbutyraldehyde was detected in this gas). Aliquots of silica were taken, slurred in methanol, and the methanol extract analyzed by GC. After one day, under these conditions, a 71% conversion was observed. When the reaction time was extended to 3 days instead of one, the percent conversion of the rearrangement increased to an average of 94% (84.4; 91.5; 100; 100%).

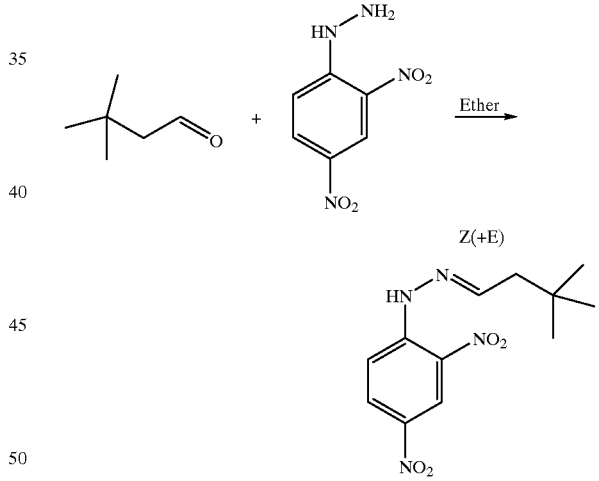

The formation of 3,3-dimethylbutyraldehyde was further confirmed by converting it to the 2,4-dinitro-phenyl hydrazine derivate. The melting point and Nuclear Magnetic Resonance (NMR) spectroscopic analysis conformed with that reported in the literature (Puterbaugh, W.H. and Newman, M. S., J. Am. Chem. Soc. 79, 3469 (1957).

Other variations and modifications of this invention will be obvious to those skilled in this art. This invention is not to be limited except as set forth in the following claims.

What is claimed is:

1. A method for preparing 3,3-dimethylbutyraldehyde comprising the step of isomerizing vaporized 3,3-dimethyl-1,2-epoxybutane in the presence of silica gel at a temperature and pressure effective to form said 3,3-dimethylbutyraldehyde.

2. A method according to claim 1, wherein said silica gel is a grade 60 silica gel.

3. A method according to claim 2, wherein said silica gel has a mesh size in a range from about 70 to about 230.

4. A method according to claim 1, wherein said step of isomerization is conducted at a temperature of about 200° C. to about 400° C.

5. A method according to claim 4, wherein the step of isomerization is conducted at a pressure of about 500 psi to about 850 psi.

6. A method according to claim 1, wherein said step of isomerization is conducted for about 2 to about 72 hours.

7. A method for preparing 3,3-dimethylbutyraldehyde comprising the steps of:
(a) oxidizing dimethylbutene to form 3,3-dimethyl-1,2-epoxybutane; and
(b) vaporizing and isomerizing said 3,3-dimethyl-1,2-epoxybutane in the presence of silica gel at a temperature and pressure effective to form said 3,3-dimethylbutyraldehyde.

8. A method according to claim 7, wherein said oxidizing step is conducted in the presence of oxygen, peroxide, dimethyldioxirane, NaOCl or a peracid.

9. A method according to claim 7, wherein said step of isomerization is conducted at a temperature of about 200° C. to about 400° C.

10. A method according to claim 9, wherein the step of isomerization is conducted at a pressure of about 500 psi to about 850 psi.

11. A method according to claim 10, wherein said step of isomerization is conducted for about 2 to about 72 hours.

12. A method according to claim 8, wherein said oxidizing step is initiated at a temperature of about −5° C. to about 0° C. and conducted at a temperature in a range of about 22° C. to about 25° C.

13. A method according to claim 12, wherein said oxidizing step is conducted for about 24 hours.

\* \* \* \* \*

UNITED STATES PATENT AND TRADEMARK OFFICE
CERTIFICATE OF CORRECTION

PATENT NO. : 5,973,209
DATED : October 26, 1999
INVENTOR(S) : INDRA PRAKASH ET AL.

It is certified that error appears in the above-identified patent and that said Letters Patent is hereby corrected as shown below:

COLUMN 3

Line 8, "Generally," should read --¶ Generally,--.

COLUMN 4

Line 26, "slurred" should read --slurried--.

Signed and Sealed this

Nineteenth Day of December, 2000

Attest:

Q. TODD DICKINSON

Attesting Officer

Commissioner of Patents and Trademarks